United States Patent [19]
Silverstein

[11] Patent Number: 5,695,491
[45] Date of Patent: Dec. 9, 1997

[54] ENDOSCOPIC ACCESSORY AND CONTAINMENT SYSTEM

[75] Inventor: Fred E. Silverstein, Seattle, Wash.

[73] Assignee: Washington Research Foundation, Seattle, Wash.

[21] Appl. No.: 343,782

[22] Filed: Nov. 22, 1994

[51] Int. Cl.⁶ .............................. A61B 1/00; A61B 19/00
[52] U.S. Cl. .................................. 606/1; 600/104
[58] Field of Search ..................... 604/95, 159, 163, 604/171, 263, 317, 403; 606/1, 110, 113, 114, 205; 600/104, 119, 121–125

[56] References Cited

U.S. PATENT DOCUMENTS

| | | |
|---|---|---|
| 2,958,364 | 11/1960 | Thompson . |
| 3,162,190 | 12/1964 | Del Gizzo . |
| 3,426,749 | 2/1969 | Jephcott . |
| 3,750,875 | 8/1973 | Juster . |
| 3,797,734 | 3/1974 | Fleury et al. . |
| 3,835,854 | 9/1974 | Jewett ................................ 604/159 |
| 3,861,395 | 1/1975 | Taniguchi . |
| 4,065,816 | 1/1978 | Sawyer . |
| 4,182,478 | 1/1980 | Etes . |
| 4,230,115 | 10/1980 | Walz, Jr. et al. . |
| 4,254,762 | 3/1981 | Yoon . |
| 4,299,244 | 11/1981 | Hirai . |
| 4,327,735 | 5/1982 | Hampson . |
| 4,329,995 | 5/1982 | Anthracite . |
| 4,487,489 | 12/1984 | Takamatsu ......................... 600/104 |
| 4,519,385 | 5/1985 | Atkinson et al. . |
| 4,550,440 | 10/1985 | Rico . |
| 4,593,699 | 6/1986 | Poncy et al. . |
| 4,620,527 | 11/1986 | Adams, Jr. . |
| 4,721,097 | 1/1988 | D'Amelio . |
| 4,754,877 | 7/1988 | Johansson et al. . |
| 4,757,381 | 7/1988 | Cooper et al. . |
| 4,772,275 | 9/1988 | Erlich ................................ 604/280 |
| 4,787,753 | 11/1988 | Barnhart . |
| 4,825,850 | 5/1989 | Opie et al. . |
| 4,886,049 | 12/1989 | Darras . |
| 4,907,395 | 3/1990 | Opie et al. . |
| 4,974,580 | 12/1990 | Anapliotis . |
| 4,976,697 | 12/1990 | Walder ............................... 604/171 |
| 4,997,084 | 3/1991 | Opie et al. . |
| 5,201,908 | 4/1993 | Jones ................................. 600/125 |
| 5,312,391 | 5/1994 | Wilk .................................. 606/205 |
| 5,417,697 | 5/1995 | Wilk et al. ........................ 606/113 |

FOREIGN PATENT DOCUMENTS 1305900  4/1992  Canada .

Primary Examiner—Glenn K. Dawson
Attorney, Agent, or Firm—Seed and Berry LLP

[57] ABSTRACT

A therapeutic or diagnostic accessory and containment system for use with a flexible or rigid endoscope during an endoscopic procedure. The system includes an accessory and a containment enclosure, wherein the accessory has an elongated, flexible, and axially-rigid shaft shaped to fit into the endoscope's biopsy channel and a tool connected to the shaft's distal end. The enclosure is adapted to contain at least a major portion of the shaft is remote from the endoscope and has at least one aperture through which the distal end of the shaft extends. An instrument deploying mechanism connected to the enclosure and to the shaft has a withdrawing mechanism that withdraws the shape into the enclosure through the aperture. A control mechanism for controlling the tool is attached to the proximal end of the shaft. The accessory can be disposable or reusable and is used in conjunction with an endoscope to perform an endoscopic procedure. The method includes inserting the shaft into a patient through the endoscope's insertion tube, performing a predetermining procedure, withdrawing the shaft and tool from the insertion tube, and immediately containing the shaft within the disposable enclosure. Thereafter, the accessory may be disposed of or cleaned, disinfected, and/or sterilized.

12 Claims, 3 Drawing Sheets

ENDOSCOPIC ACCESSORY AND CONTAINMENT SYSTEM

FIELD OF THE INVENTION

This invention relates to the field of endoscopy, and more particularly, to a system for controlling and containing the shaft and tool of an endoscopic accessory.

BACKGROUND OF THE INVENTION

The use of endoscopes for diagnostic and therapeutic indications is rapidly expanding. To improve performance, endoscopes have been optimized to best accomplish their purpose. Therefore, there are upper endoscopes for examination of the esophagus, stomach and duodenum; colonoscopes for examining the colon; angioscopes for examining blood vessels; bronchoscopes for examining the bronchi; laparoscopes for examining the peritoneal cavity; and arthroscopes for examining joint spaces. The discussion which follows will apply to all of these types of endoscopes, whether rigid or flexible.

Instruments to examine the rectum and sigmoid colon, known as flexible sigmoidoscopes, are good examples of the usefulness of endoscopic technology. These devices are expensive, and they are used in a contaminated environment for a procedure which is brief (5–10 minutes) and where problems of cleaning time and contamination are important factors. There has been a large increase in the use of the "flexible sigmoidoscope" for use in screening symptomatic and asymptomatic patients to prevent colon and rectal cancer.

Typically, these endoscopes have a flexible insertion tube with multiple small channels that extend along the length of the endoscope and come into contact with body tissues and fluids. These channels allow air insufflation, water flow to wash the tip, and biopsy and suction. Endoscopic accessories that, for example, take a biopsy of tissue samples, are often inserted through at least one of the channels during an endoscopic procedure. As a result, the accessories are grossly contaminated with, for example, blood, stool, mucus, or tissue when removed from the endoscope.

These endoscopic accessories have elongated flexible shafts and a tool, such as forceps, operatively connected to the shaft's distal end. To extend through the endoscope's biopsy channel, the shaft must be longer than the endoscope; for example, in colonoscopy, the colonoscope's shaft is up to two meters long. Although the shaft is preferably resilient, in some cases it must have sufficient stiffness that the rotational and axial positions of the distal end can be controlled by manipulating the proximal end. Furthermore, the accessory must also allow the physician to control the accessory's tool from the shaft's proximal end when the shaft and tool are extended into a patient. As a result of its length and stiffness, the shaft tends to flop around or suddenly move about uncontrollably when the accessory is removed from the endoscope. Unacceptable contamination occurs when the flopping shaft touches equipment, the patient, physicians, or nurses or when a physician or nurse grabs the shaft in an attempt to control the unwieldy instrument.

In addition, an accessory may be contaminated prior to insertion into a patient if the shaft flops around and touches contaminated equipment or is grabbed by a person having contaminants on their gloved hands. Accordingly, an accessory that is difficult to manage or control before, during, and after an endoscopic procedure increases the risk of unacceptable contamination.

DISCLOSURE OF THE INVENTION

It is an object of the invention to provide a therapeutic or diagnostic accessory and containment system for use with an endoscope that contains the accessory's shaft when it is not inserted into an endoscope, thereby greatly reducing the risk of contamination.

It is another object of the present invention to provide a therapeutic or diagnostic accessory and containment system having an enclosure for containing, in a compact manner, the associated shaft before insertion into and immediately after removal from an endoscope.

It is a further object of the present invention to provide an endoscopic accessory having an enclosure and a withdrawing mechanism that allows withdrawal of the accessory's long shaft from the endoscope without a physician or nurse having to touch the shaft.

It is a further object of the present invention to provide an endoscopic system that has an endoscope in combination with a therapeutic or diagnostic accessory and containment system having an enclosure for containing the accessory's long shaft immediately after being removed from the endoscope.

It is another object of the present invention to provide an endoscopic system that has an advancing mechanism that allows an accessory to be advanced into a visual field and be opened and closed or otherwise activated.

It is another object of the present invention to provide a method of performing an endoscopic procedure wherein the endoscopic accessory and associated shaft and work tool are contained in an enclosure immediately upon withdrawal from the endoscope.

These and other objects of the invention are provided by a therapeutic or diagnostic accessory and containment system used with an endoscope having a flexible or rigid insertion tube containing a biopsy channel, the system having an accessory with an elongated, flexible shaft with proximal and distal ends, the shaft being shaped to fit into the biopsy channel, and a tool connected to the shaft's distal end. An enclosure is provided to contain at least a major portion of the shaft, wherein the enclosure is remote from the endoscope and has at least one aperture through which the distal end of the shaft extends. The enclosure is coupled to an instrument deploying mechanism that has a withdrawing mechanism to withdraw the shaft into the enclosure through the aperture. The shaft is preferably a resilient shaft having axial rigidity that can be pushed through the endoscope and positioned as needed within the patient. The shaft connects to a control mechanism that is operatively attached to the tool and allows a physician or nurse to control the tool before, during, or after an endoscopic procedure. In a particular embodiment of the invention, the system or parts thereof are disposable.

The therapeutic or diagnostic accessory and containment system is used with an endoscope in an endoscopic procedure wherein the flexible shaft is advanced through the biopsy channel of an endoscope and past its distal end, and an endoscopic procedure is performed with the tool inserted in the body of a patient. The shaft is then withdrawn by the withdrawing mechanism from the endoscope and immediately contained in the enclosure. The contaminated accessory or parts thereof are then disposed of in a proper receptacle, or when appropriate, taken to a cleaning room to be cleaned and then sterilized or disinfected.

Further objects and advantages of the subject invention will become apparent from the following detailed description of the preferred embodiment taken in conjunction with the drawings.

DETAILED DESCRIPTION OF THE PREFERRED EMBODIMENT

Figure 1:
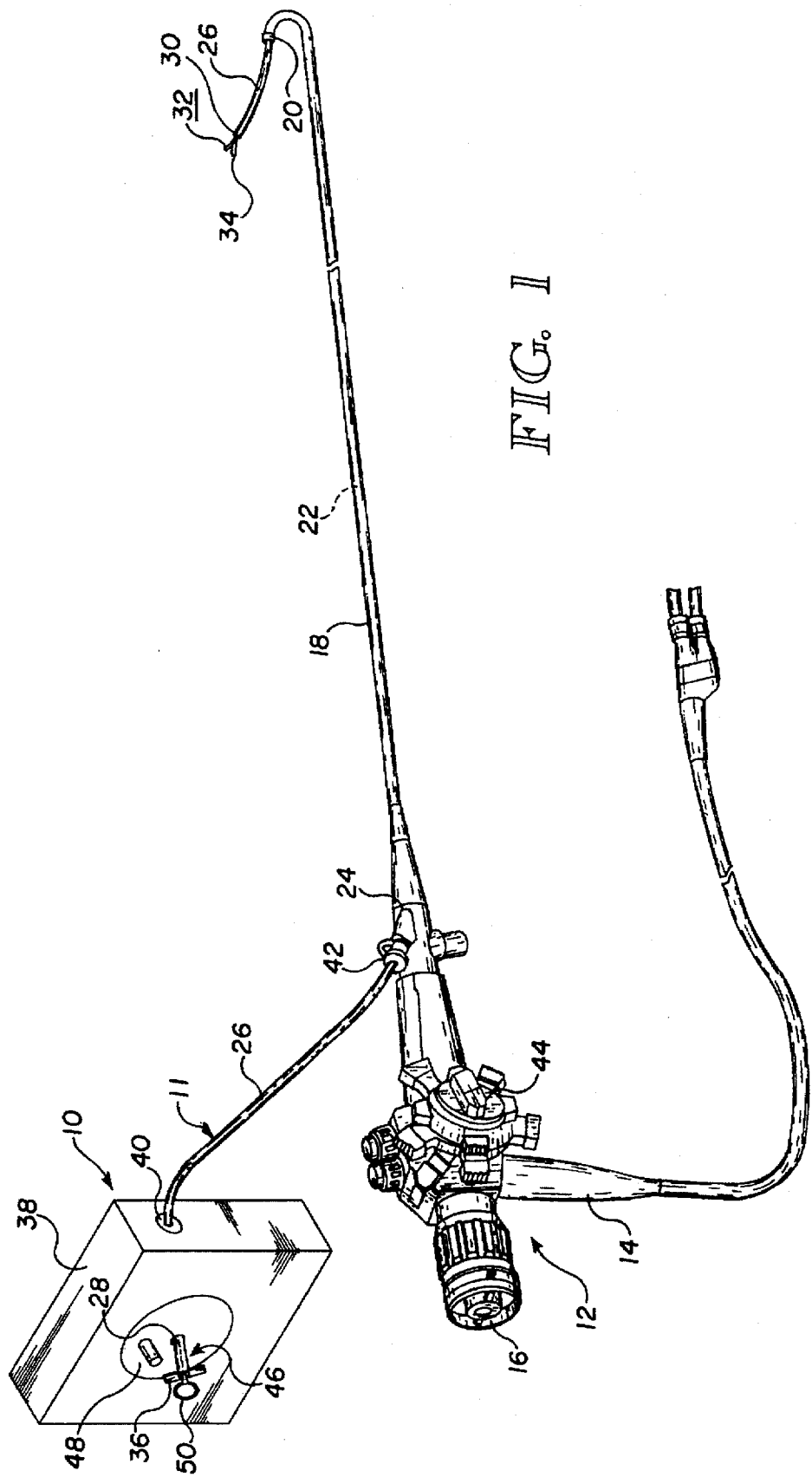
FIG. 1 is an isometric view of the therapeutic or diagnostic endoscopic accessory and containment system in accordance with the present invention showing the accessory in combination with an endoscope.

As best seen in FIG. 1, a therapeutic or diagnostic accessory and enclosure assembly and containment system 10, in accordance with the present invention, includes an endoscopic accessory 11 and is used in conjunction with a conventional endoscope 12 having a handle 14, an eye piece 16 connected to the handle 14, and an elongated, flexible insertion tube 18. As is well known in the art, the insertion tube 18 is inserted into a patient's body cavity, and light emitted from the distal end 20 of the insertion tube 18 illuminates tissues in the cavity. The image viewed through the tubes distal end 20 is conveyed to the endoscope handle 14, either through an internal fiber optic bundle or electronically from a miniature television camera mounted at the tube's distal end 20. Accordingly, the physician may see the area that he or she is manipulating.

The endoscope's insertion tube 18 normally includes internal channels that extend the length of the insertion tube and terminate at openings in the tube's distal end 20. These channels are typically used for suctioning fluids from the body cavity, or inserting air into the body cavity and for spraying water onto a lens at the distal end 20, in order to clean the lens. The insertion tube 18 further includes at least one biopsy channel 22 that extends from the tube's proximal end 24 to the distal end 20, and allows a physician to take biopsies. The insertion tube 18 can have multiple working channels, including the biopsy channel, that each receive an accessory 11. On the other hand, the biopsy channel may be sized so as to simultaneously receive more than one accessory 11.

The system 10 includes an accessory 11 that has an elongated, flexible shaft 26 of conventional design with a proximal end 28 and a distal end 30. The shaft is similar to a conventional endoscopic accessory shaft and is shaped to fit into the biopsy channel 22. A tool 32, such as forceps 34, operatively connects to the shaft's distal end 30 and is used during an endoscopic procedure. A tool control mechanism 36 is connected to the shaft's proximal end 28 and allows an operator to control the tool 32 in the event that the tool includes movable components such as the jaws of forceps. In the preferred embodiment, the control mechanism 36 is a plunger device 38 that is operatively connected to the forceps 34 by internal control wires. Thus, the plunger 38 enables a physician to control and operate the forceps 34 in a desired manner while the shaft 26 is extended into a patient. However, the tool 32 may also be a biopsy probe, an ultrasound transducer, a microwave heater, etc., in which case the tool control mechanism 36 may be omitted.

The shaft 26 and forceps 34 enter the biopsy channel 22 through a biopsy channel inlet 42 at the tube's proximal end 24. A physician controls the exact positioning of the insertion tube 18 within a body cavity with control wheels 44 connected to the endoscope's handle 14 and by extending or withdrawing the shaft 26 into or out of the biopsy channel 22. The wheels 44 are operatively connected to the tube's distal end 20 by control wires that allow the distal end 20 to be moved up, down, left, right, or any combination thereof. Thus, when the shaft 26 and forceps 34 are extended beyond the tube's distal end 20, the tool's position with respect to the patient's internal cavities is controlled by adjusting the control wheels 44 and by extending or withdrawing the shaft 26.

In order to work in conjunction with the insertion tube 18, the shaft 26 is made of a resilient material that will freely bend along with the flexible insertion tube. Alternatively, the shaft 26 can also be rigid. The resilient shaft 26 must also be rigid enough to resist bending forces applied to the tool when it is extended beyond the tube's distal end 20. The shaft 26 further has axial rigidity that allows the shaft 26 to extend beyond the tube's distal end 20 when the shaft is pushed further into the biopsy channel. Without this axial rigidity, the physician would not have sufficient control of the tool, and any attempt to extend the shaft 26 beyond the tube's distal end 20 would be like pushing axially on a string. Thus, the shaft's resiliency and axial rigidity allow the physician to accurately and efficiently control the tool's longitudinal position within the patient's body.

The system 10 also includes an enclosure 39 that is adapted to contain at least a major portion of the accessory 11 before, during or after an endoscopic procedure. The enclosure is remotely located from the endoscope 12, such that contamination of the enclosure will not necessarily result in contamination of the endoscope. The enclosure 39 may be any type of a bag or box-like container that is sufficient to contain the major portion of the shaft 26. The enclosure 39 has an aperture 40 through which the shaft 26 is withdrawn or advanced. In addition, the enclosure 39 includes an instrument deploying mechanism 46, such as a crank device 48, that acts to extend the distal portion of the shaft 26 into the biopsy channel 22 and, after an endoscopic procedure has been completed, to withdraw the shaft back into the enclosure through the aperture 40. Since the shaft 26 and forceps 34 may be moved into and out of the enclosure 39 several times during an endoscopic procedure and fully withdrawn into the enclosure 39 upon completion of the procedure, the contaminated shaft 26 is contained in a compact and sanitary manner, thereby greatly reducing the risk of contaminating personnel and equipment. Hence, a physician may withdraw the shaft 26 into the enclosure a predetermined distance without having to touch the shaft 26 by rotating the crank device 48.

After an endoscopic procedure has been completed, the shaft 26 is drawn completely into the enclosure 39, thereby eliminating the risk of contaminating persons or equipment by a flopping, uncontrolled, contaminated shaft. The ability to withdraw a grossly contaminated shaft without having to touch it effectively reduces the risk of contaminating the endoscope, other equipment, physicians, nurses, or the patient. The accessory 11 also reduces the burden and cost of cleaning the accessory because it is disposable. Thus, the shaft 26 may be contained within the enclosure 39, and the entire accessory 11 or parts thereof may be disposed of in a proper medical waste receptacle. Alternatively, the shaft 26 can be held in the enclosure 39 until the accessory 11 is taken to a cleaning area to be cleaned, disinfected and/or sterilized. Thereafter the accessory 11 may be reused.

The illustrated embodiment of the system 10 has a single accessory 10 with a single shaft 26. However, the system 10 can be adapted to include, for example, multiple accessories (not illustrated) within the enclosure 39 wherein the shafts 26 are movably positioned in either a single working channel within the insertion tube 18 or within multiple working channels in the insertion tube so as to allow the physician to use the different accessories with a single enclosure for different portions of an endoscopic procedure.

Figure 2:
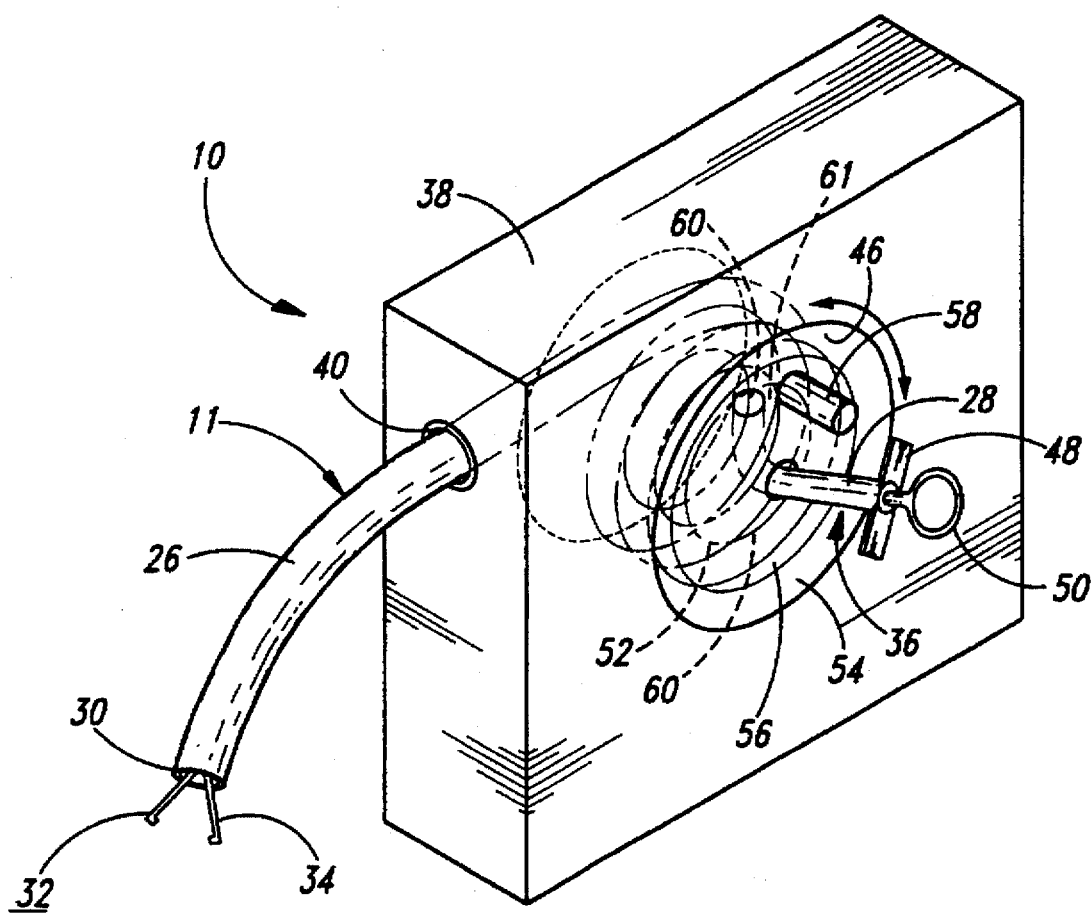
FIG. 2 is an enlarged isometric view of the accessory and containment system of FIG. 1 wherein the shaft is partially extended out of an enclosure.

As best seen in FIG. 2, the instrument deploying mechanism 46 includes a crank device 48 made up of a cylindrical drum 52 connected to larger diameter outer flanges 54 that, in turn, are rotatably connected to the enclosure 39. The drum 52 is disposed within the enclosure portion 38 and pierces the enclosure at apertures 56 having substantially the same cross-sectional area as the drum 52. The drum 52 connects to the flanges 54 at the aperture 56, such that the flanges 54 are on the outside of the enclosure 39. A crank handle 58 is pivotably mounted on the outer wall of a flange 54 whereby a user can grasp the handle and rotate the flanges 54 and drum 52 about their longitudinal axis. The drum 52 is a hollow member having a bore 60 in the axial wall 61, wherein the bore 60 receives the shaft 26. The proximal end 28 of the shaft 26 extends through the bore 60 and connects to the plunger device 38. The plunger device 38 is perpendicularly oriented to and carried by one of the flanges 54 and is coaxially aligned with the drum 52 and flanges 54. Thus, upon rotating the crank device 48, the drum 52 and the flanges 54 rotate and wind the shaft 26 about the drum 52. In an alternative embodiment of the invention, the plunger device 38 is rotatably coupled to the flange 54 such that the plunger device 38 can rotate about its longitudinal axis notwithstanding rotation of the drum 52 and flanges 54. As a result, the operator does not have to remove his hand from the plunger device 38 when winding the crank device 48.

To support the instrument deploying mechanism 46, the preferred enclosure 39 is a thin-walled, substantially rectangular box having sufficient rigidity to stand and support the instrument deploying mechanism 46 while remaining lightweight and manageable. In addition, the box may be substantially transparent so the internal components are visible to the user.

Figure 3:
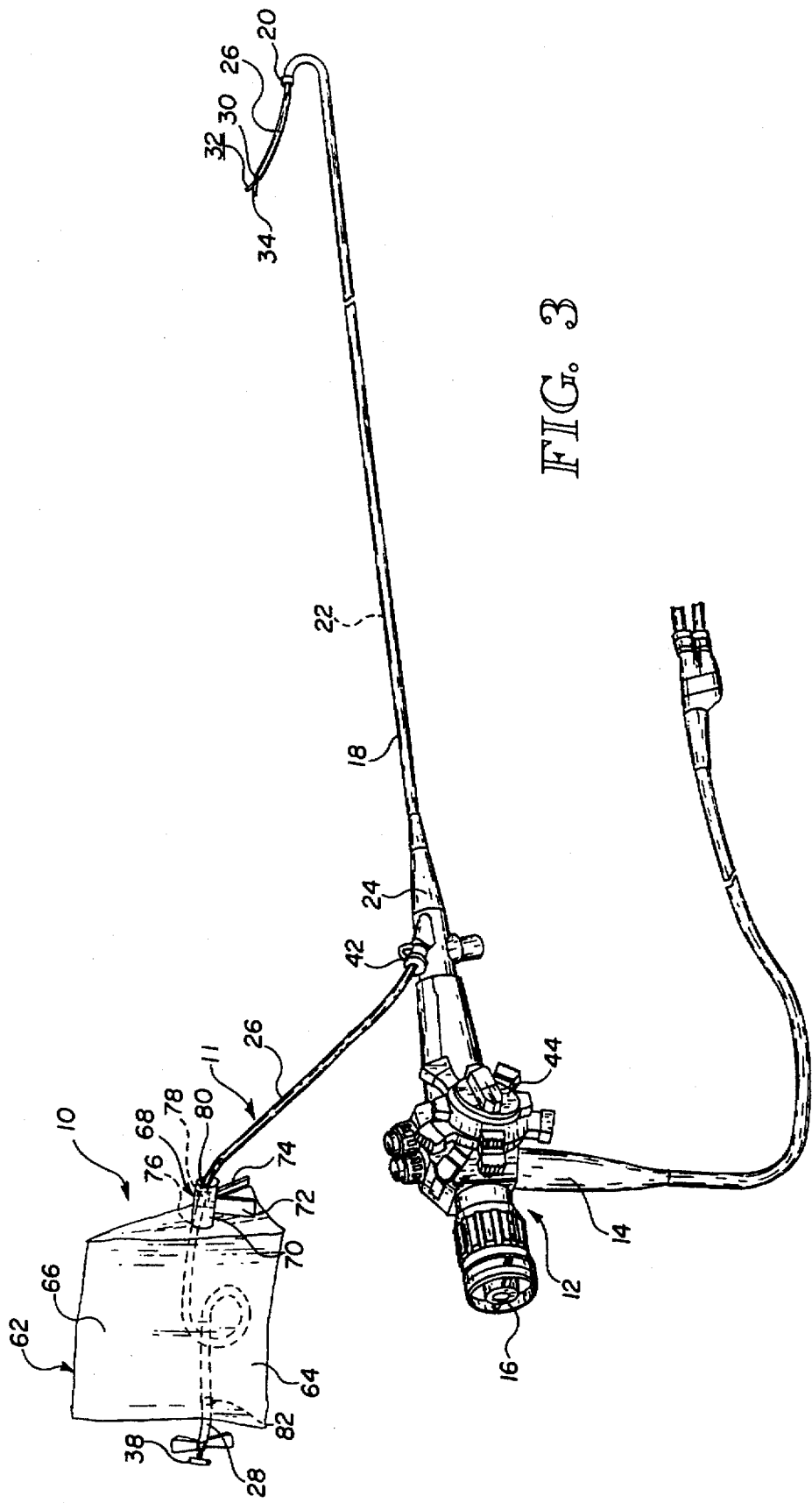
FIG. 3 is an isometric view of an alternate embodiment of the therapeutic or diagnostic endoscopic accessory and containment system in accordance with the present invention, showing the accessory in combination with an endoscope.

As seen in FIG. 3, an alternative embodiment of the therapeutic or diagnostic accessory and containment system 10 is shown wherein the elongated, flexible shaft 26 of the accessory 11 is coupled to an enclosure 62 that is remotely located from the endoscope 12 and is adapted to contain at least a major portion of the shaft 26. For ease of understanding, the components of this alternative embodiment will be similarly numbered with the first embodiment when of a similar construction. Only the differences in construction will be described in detail.

The preferred enclosure 62 is a bag, which is easily and inexpensively manufactured, having a supporting base 64 and sidewalls 66 that are rigid enough to support an instrument deploying mechanism 68. The instrument deploying mechanism 68 is made up of a housing 70 connected to a grip or handle 72 and coupled to a spring-biased activating lever 74 that may be squeezed by an operator to draw the lever adjacent to the handle. The instrument deploying mechanism 68 is connected to the enclosure 62 through an aperture 76 such that the housing 70 is carried by and sealed to the enclosure 62. As the operator releases the lever 74, the biasing spring returns the lever to its starting position. The lever 74 is also connected to a shaft moving device 78 that engages the shaft such that when the lever 74 is squeezed, the shaft moving device 78 pushes or pulls the shaft 26 longitudinally within a bore 80 through the housing 70. The shaft moving device 78 may be configured such that it acts as a shaft withdrawing mechanism or a shaft advancing mechanism, or both. The advancing mechanism acts to draw the shaft 26 out of the enclosure 62 and advance it a predetermined increment into or through the biopsy channel 22. Similarly, the withdrawing mechanism acts to pull the shaft 26 into the enclosure 62 at an incremental distance, Accordingly, the shaft 26 may be advanced and withdrawn through the aperture 76 when the shaft is moved along the longitudinal axis of the housing 70 by the physician without touching the shaft.

The instrument deploying mechanisms discussed above are manual mechanisms. In an alternate embodiment not illustrated, the instrument deploying mechanism 68 includes an automatic deploying unit having, for example, a motorized unit that is connected to the enclosure and to the shaft. Upon activation, the motorized unit advances or withdraws the shaft longitudinally through the biopsy channel. The automatic deploying unit includes a manual override, so the shaft can be also be advanced or retracted manually.

The shaft's proximal end 28 extends through a second aperture 82 in the enclosure 62 and is secured to the enclosure such that the plunger device 38 remains connected to the shaft 26 and operatively connected to the forceps 34. The plunger device 38 remains on the exterior of the enclosure 62 and is accessible by the physician during an endoscopic procedure. In the preferred embodiment, the enclosure 62 is sufficiently rigid to support the activation system 68 and the plunger device 38 in a position that provides the user with easy access to the exterior components. In addition, the preferred enclosure 62, shaft 26, and tool 32 may be disposable. The instrument activation system 68 and plunger device 38 may also be disposable such that, upon completion of the endoscopic procedure and withdrawal of the shaft 26 into the enclosure 62, the entire accessory 11 disposed of in a proper medical waste receptacle.

Referring to FIGS. 1 and 2, the accessory 11 is used during an endoscopic process along with the endoscope 12 wherein the accessory contains the flexible shaft 26 and tool 32 prior to insertion into the endoscope. Upon insertion, the tool 32 and the shaft's distal end 30 are advanced through the endoscope's biopsy channel 22 and beyond the tube's distal end 20 to a predetermined position. The shaft's distal end 30 may be advanced into the biopsy channel by the physician grabbing the shaft 26 and physically pushing it through the biopsy channel inlet 42 or by a deploying mechanism 68 (as seen in FIG. 3) such that the shaft 26 incrementally advances into the biopsy channel 22 without being physically touched by the physician. Once the shaft 26 is inserted and advanced, the physician performs an endoscopic procedure with the tool 32. The tool 32 and shaft 26 are then withdrawn from the biopsy channel 22 directly into the enclosure 39, whereby the withdrawn portion of the shaft is contained within the enclosure. Withdrawing the shaft 26 may be accomplished by rotating the crank device 48 described above or squeezing the activating lever 74 of the alternate embodiment until the shaft 26 is partially or completely contained in the enclosure, depending upon the stage of the endoscopic procedure. Upon completion of the procedure and complete containment of the shaft 26, the enclosure 39, shaft 26, and tool 32 may then be disposed of into a suitable receptacle. In an alternate embodiment, the enclosure 39, shaft 26, and/or tool 32 may be removed to a suitable area to be cleaned, disinfected, and/or sterilized.

Numerous modifications and variations of the endoscopic accessory and containment system disclosed herein will occur to those skilled in the art in view of this disclosure. For example, different enclosure configurations and different instrument deploying mechanisms could obviously be used. In fact, the instrument deploying mechanism could be omitted since the physician is normally able to grab the shaft 26 and move it axially. Therefore, it is to be understood that these modifications and variations, and equivalents thereof, may be practiced while remaining within the spirit and the scope of the invention as defined in the following claims.

We claim:

1. A therapeutic or diagnostic accessory and containment system used with an endoscope having an insertion tube containing a biopsy channel, comprising:

an accessory having an elongated, flexible shaft having a proximal end and a distal end, said shaft being shaped to fit into the biopsy channel of the endoscope;

a tool connected to said shaft at said distal end;

an enclosure adapted to contain at least a major portion of said shaft, said enclosure having a least one aperture through which the distal end of said shaft is extended and retracted for insertion into the biopsy channel and withdrawal from the biopsy channel; and an instrument deploying mechanism coupled to said enclosure and to said shaft, said deploying mechanism comprising a withdrawing mechanism that withdraws said shaft into said enclosure through said aperture, said shaft having a control mechanism for controlling said tool, said control mechanism being attached to said deploying mechanism and operatively connected to said tool.

2. The therapeutic or diagnostic accessory and containment system of claim 1, further comprising an advancing mechanism that advances said shaft out of said enclosure through said aperture.

3. The therapeutic or diagnostic accessory and containment system of claim 1 wherein said deploying mechanism comprises a crank system connected to said shaft and rotatably coupled to said enclosure.

4. The therapeutic or diagnostic accessory and containment system of claim 1 wherein said deploying mechanism comprises a control handle, said control handle carrying said withdrawing mechanism.

5. The therapeutic or diagnostic accessory and containment system of claim 1 wherein said shaft has a control mechanism for controlling said tool, said control mechanism attached to said proximal end of said shaft and operatively connected to said tool.

6. An endoscopic system used during an endoscopic procedure, the system comprising:

an endoscope having an insertion tube with a first proximal end, a first distal end, a biopsy channel extending through said insertion tube from said first proximal end to said first distal end, and a biopsy channel inlet at said first proximal end;

a therapeutic or diagnostic accessory and containment assembly used with said endoscope during an endoscopic procedure, said assembly comprising:

an accessory having an elongated flexible shaft of a predetermined length having a second proximal end, a second distal end, and a tool connected to said second distal end, said tool and said second distal end shaped to extend into said biopsy channel through said channel inlet;

an enclosure adapted to contain at least a major portion of said shaft and being sized larger than the biopsy channel inlet so that the enclosure is too large to fit into the biopsy channel, said enclosure being remote from said endoscope and having at least one aperture through which said shaft can be advanced and withdrawn for insertion and removal from the biopsy channel while the enclosure remains exterior of the biopsy channel; and an instrument deployment mechanism coupled to said enclosure and to said shaft, said instrument deployment mechanism comprising a withdrawing mechanism to withdraw said shaft from said biopsy channel directly into said enclosure through said aperture.

7. The endoscopic system of claim 6 wherein said instrument deployment mechanism further comprises an advancing mechanism to advance said shaft out of said enclosure through said aperture.

8. The endoscopic system of claim 6 wherein said shaft has a control mechanism for controlling said tool, said control mechanism attached to said deployment mechanism and operatively connected to said tool.

9. The endoscopic system of claim 6 wherein said deployment mechanism comprises a crank system connected to said shaft and rotatably connected to said enclosure.

10. The endoscopic system of claim 6 wherein said deployment mechanism comprises a control handle, said control handle carrying said withdrawing mechanism.

11. The endoscopic system of claim 9 wherein said shaft has a control mechanism for controlling said tool, said control mechanism coupled to said proximal end of said shaft and operatively connected to said tool.

12. The endoscopic system of claim 9 wherein the insertion tube of said endoscope is a flexible insertion tube.

* * * * *